US008970687B2

(12) United States Patent
Fueki et al.

(10) Patent No.: US 8,970,687 B2
(45) Date of Patent: Mar. 3, 2015

(54) MEDICAL INFORMATION MANAGEMENT APPARATUS AND MEDICAL INFORMATION MANAGEMENT SYSTEM

(71) Applicant: Olympus Medical Systems Corp., Tokyo (JP)

(72) Inventors: Norio Fueki, Tokyo (JP); Hitoshi Suzuki, Tokyo (JP); Emiko Ouchi, Tokyo (JP); Chieko Watanabe, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/064,682

(22) Filed: Oct. 28, 2013

(65) Prior Publication Data

US 2014/0118517 A1    May 1, 2014

Related U.S. Application Data

(63) Continuation of application No. PCT/JP2013/002570, filed on Apr. 16, 2013.

(30) Foreign Application Priority Data

Jun. 20, 2012    (JP) .................................. 2012-139154

(51) Int. Cl.
*A62B 1/04*    (2006.01)
*A61B 1/04*    (2006.01)
(Continued)

(52) U.S. Cl.
CPC ............... *A61B 1/04* (2013.01); *A61B 1/00006* (2013.01); *A61B 1/00009* (2013.01); *G06Q 50/22* (2013.01); *A61B 1/00039* (2013.01); *A61B 1/00045* (2013.01); *G06Q 10/0631* (2013.01)

USPC .................. 348/65; 348/77; 705/2; 705/3

(58) Field of Classification Search
CPC .......... A61B 1/041; A61B 10/02; A61B 1/31; A61B 1/018; A61B 1/05; A61B 5/42; A61B 1/00045; A61B 5/742; G06T 2207/10068; G06T 2207/30004; G06T 2207/30028
USPC ....... 382/128, 162; 600/101; 604/66; 348/45, 348/65, 77; 345/589; 705/2, 3
See application file for complete search history.

(56) References Cited

U.S. PATENT DOCUMENTS 6,677,983 B1 *   1/2004   Takahashi et al. .............. 348/65
8,310,529 B2 *   11/2012  Krupnick et al. ............... 348/65
(Continued)

FOREIGN PATENT DOCUMENTS

JP     2000-081577 A    3/2000
JP     2001-128993 A    5/2001
(Continued)

*Primary Examiner* — Sath V Perungavoor
*Assistant Examiner* — Nathnael Aynalem
(74) *Attorney, Agent, or Firm* — Scully, Scott, Murphy & Presser, P.C.

(57) ABSTRACT

An order storage unit stores an order for a medical practice to be performed using an endoscopic system. A control unit transmits an order to the endoscopic system via a communication line and also transmits device setting information linked to at least one of a doctor and a medical practice type specified by the order. When the control unit receives a notification of a change from the endoscopic system while the medical practice specified by the order is being performed, the control unit transmits new device setting information corresponding to the change to the endoscopic system.

4 Claims, 12 Drawing Sheets

(51) Int. Cl.
*A61B 1/00* (2006.01)
*G06Q 50/22* (2012.01)
*G06Q 10/06* (2012.01)

(56) References Cited

U.S. PATENT DOCUMENTS

| | | |
|---|---|---|
| 8,472,682 B2 * | 6/2013 | Guissin et al. ............... 382/128 |
| 2001/0015754 A1 * | 8/2001 | Nakashima et al. ............ 348/65 |
| 2006/0047184 A1 * | 3/2006 | Banik et al. .................. 600/156 |
| 2006/0184407 A1 * | 8/2006 | Ozaki et al. ....................... 705/7 |
| 2007/0088193 A1 * | 4/2007 | Omori et al. .................. 600/101 |

FOREIGN PATENT DOCUMENTS

| | | |
|---|---|---|
| JP | 2008-529161 A | 7/2008 |
| JP | 2010-213871 A | 9/2010 |
| JP | 2011-186802 A | 9/2011 |
| WO | WO 2008061833 A1 * | 5/2008 |

\* cited by examiner

FIG.3

| ORDER NUMBER | PATIENT INFORMATION | | | | SCHEDULED EXAM DATE AND TIME | DOCTOR | EXAMI-NATION ROOM | MEDICAL PRACTICE TYPE | STATUS | ... |
| --- | --- | --- | --- | --- | --- | --- | --- | --- | --- | --- |
| | PATIENT ID | NAME | DATE OF BIRTH | AGE | SEX | | | | | |
| 1 | 003242 | ICHIRO SATO | 1976/9/23 | 35 | MALE | 2012/6/8 7:30 | TANAKA | EXAMI-NATION ROOM 2 | UPPER ENDOSCOPIC EXAMINATION | PER-FORMED | ... |
| 2 | 000921 | JIRO SUZUKI | 1966/8/04 | 45 | MALE | 2012/6/8 10:00 | YAMAMOTO | EXAMI-NATION ROOM 1 | LOWER ENDOSCOPIC EXAMINATION | NOT PER-FORMED YET | ... |
| 3 | 020984 | SABURO TAKAHASHI | 1957/7/11 | 54 | MALE | 2012/6/8 10:00 | TANAKA | EXAMI-NATION ROOM 2 | UPPER ENDOSCOPIC EXAMINATION | NOT PER-FORMED YET | ... |
| 4 | 009423 | SHIRO WATANABE | 1984/9/29 | 27 | MALE | 2012/6/8 13:00 | | EXAMI-NATION ROOM 2 | UPPER ENDOSCOPIC EXAMINATION | NOT PER-FORMED YET | ... |
| ... | | | | | | | | | | | |

| MASTER NUMBER | MASTER CONDITION ||||||| SETTING INFORMATION |||||||
| --- | --- | --- | --- | --- | --- | --- | --- | --- | --- | --- | --- | --- | --- | --- |
| | | | | | | | | ENDOSCOPE PROCESSING APPARATUS |||| LIGHT-SOURCE APPARATUS | PRINTING APPARATUS | |
| | DOCTOR | MEDICAL PRACTICE TYPE | ENDOSCOPE | ENDOSCOPE PROCESSING APPARATUS | LIGHT-SOURCE APPARATUS | PRINTING APPARATUS | RED-NESS | CON-TRAST | IMAGE SIZE | TERMINATION CONDITION | ... | AMOUNT OF LIGHT | ... | LAYOUT | ... |
| 1 | TANAKA | UPPER ENDOSCOPIC EXAMINATION | AA-01 (FOR GENERAL PURPOSE) | B-01 | C-01 | D-01 | +2 | 0 | LARGE | REMOVAL OF SCOPE | ... | -1 | ... | 4 | ... |
| 2 | TANAKA | UPPER ENDOSCOPIC EXAMINATION | AA-02 (FOR TREATMENT) | B-01 | C-01 | D-01 | +1 | +1 | SMALL | POWER OFF | ... | +1 | ... | 1 | ... |
| 3 | YAMADA | LOWER ENDOSCOPIC EXAMINATION | AB-02 (OPTICAL MAGNIFICATION) | B-01 | C-01 | D-01 | +1 | 0 | SMALL | POWER OFF | ... | +2 | ... | 4 | ... |
| 4 | YAMADA | ULTRASOUND EXAMINATION | AC-01 | B-01 | C-01 | D-01 | - | +2 | LARGE | REMOVAL OF SCOPE | ... | +2 | ... | 1 | ... |
| 5 | GENERAL | UPPER ENDOSCOPIC EXAMINATION | AA-01 (FOR GENERAL PURPOSE) | B-01 | C-01 | D-01 | +1 | +1 | LARGE | REMOVAL OF SCOPE | ... | 0 | ... | 1 | ... |

| ITEM | CONTENTS |
|---|---|
| DOCTOR | TANAKA |
| MEDICAL PRACTICE TYPE BEFORE CHANGE | UPPER ENDOSCOPIC EXAMINATION |
| MEDICAL PRACTICE TYPE AFTER CHANGE | UPPER ENDOSCOPIC TREATMENT |
| TIME ELAPSED | 8:39 |

FIG.7

| PREVIOUS DEVICE SETTING INFORMATION | MASTER NUMBER 24 | UPPER ENDOSCOPIC EXAMINATION (GENERAL) |
|---|---|---|
| SUBSEQUENT DEVICE SETTING INFORMATION CANDIDATE 1 | MASTER NUMBER 37 | UPPER ENDOSCOPIC EXAMINATION (DETAILED) |
| SUBSEQUENT DEVICE SETTING INFORMATION CANDIDATE 2 | MASTER NUMBER 31 | UPPER ENDOSCOPIC TREATMENT |
| SUBSEQUENT DEVICE SETTING INFORMATION CANDIDATE 3 | MASTER NUMBER 50 | ULTRASOUND EXAMINATION |
| ⋮ | | |

| PREVIOUS DEVICE SETTING INFORMATION | MASTER NUMBER 24 | UPPER ENDOSCOPIC EXAMINATION (GENERAL) |
|---|---|---|
| CURRENT SCOPE MODEL NUMBER (AFTER CHANGE) | \multicolumn{2}{c|}{AA-02 (FOR TREATMENT)} |
| SUBSEQUENT DEVICE SETTING INFORMATION CANDIDATE 1 | MASTER NUMBER 31 | UPPER ENDOSCOPIC TREATMENT (REMOVAL OF POLYP) |
| SUBSEQUENT DEVICE SETTING INFORMATION CANDIDATE 2 | MASTER NUMBER 33 | UPPER ENDOSCOPIC TREATMENT (REMOVAL OF FOREIGN SUBSTANCE) |
| ⋮ | | |

230bb

US 8,970,687 B2

MEDICAL INFORMATION MANAGEMENT APPARATUS AND MEDICAL INFORMATION MANAGEMENT SYSTEM

CROSS-REFERENCE TO RELATED APPLICATIONS

The present application is based upon and claims the benefit of priority from PCT/JP2013/002570, filed on Apr. 16, 2013, which claims benefit to Japanese Patent Application No. 2012-139154, filed on Jun. 20, 2012, the entire contents of each of which are incorporated herein by reference.

BACKGROUND OF THE INVENTION

1. Field of the Invention

The present invention relates to a medical information management apparatus and a medical information management system for managing device setting information of an endoscopic system.

2. Description of the Related Art

An endoscopic system is constituted of various devices such as an endoscope, a light-source apparatus, a display apparatus, an endoscope processing apparatus that processes images captured by the endoscope, and the like. The settings of these devices are adjusted according to the type of a medical practice in which the endoscopic system is used or to the preference of a doctor. For example, preferences for redness, enhancement, contrast, and the like of an endoscopic image displayed on the display device vary depending on doctors. Also, an eye-friendly image setting varies depending on a region of an affected part. There is a wide variety of setting items for these devices, and it is a complicated task to set or change the setting items all by hand. Regarding this, a method has been suggested that allows devices to be automatically set in advance based on medical record information of patients (for example, see Patent Document 1).

[Patent Document 1] JP 2008-529161 (published Japanese translation of PCT international publication for patent application)

If a polyp is found during an endoscopic examination and the polyp is to be removed on the spot, a medical practice type changes from an endoscopic examination to endoscopic treatment. It is necessary to connect an additional instrument or change the operation setting of an endoscope processing apparatus depending on the change. When a medical practice type is changed in the middle of a medical practice as described above, it is necessary to change the device setting of the endoscopic system. The medical practice performed on a patient is discontinued during the change of the device setting. The change of the device setting needs to be performed promptly and accurately from the aspect of reducing the burden on a patient, preventing delays in the progress, and preventing setting errors.

SUMMARY OF THE INVENTION

A medical information management apparatus according to one embodiment of the present invention is a medical information management apparatus connected to an endoscopic system via a communication line, comprising: an order storage unit configured to store an order for a medical practice to be performed using the endoscopic system; a device setting information storage unit configured to store device setting information for making a device setting of the endoscopic system; a control unit configured to transmit an order to the endoscopic system via the communication line and also to transmit device setting information linked to at least one of a doctor and a medical practice type specified by the order; and a temporary storage unit configured to temporarily store device setting change information received from the endoscopic system. When the control unit receives a notification of a change from the endoscopic system while the medical practice specified by the order is being performed, the control unit transmits new device setting information corresponding to the change to the endoscopic system. When a device setting of the endoscopic system is changed by a user's operation on the endoscopic system while the medical practice specified by the order is being performed, the control unit receives device setting change information that indicates a device setting that has been changed from the medical information management apparatus. The control unit displays on a display apparatus a screen for allowing a user to select whether or not device setting information in which the device setting change information stored in the temporary storage unit is incorporated is to be registered in the device setting information storage unit after the medical practice specified by the order is ended.

Another embodiment of the present invention relates to a medical information management system. The medical information management system is a medical information management system comprising an endoscopic system and a medical information management apparatus that are connected to a communication line, wherein the medical information management apparatus has: a first order storage unit configured to store an order for a medical practice to be performed using the endoscopic system; a device setting information storage unit configured to store device setting information for making a device setting of the endoscopic system; a first control unit configured to transmit an order to the endoscopic system via the communication line and also to transmit device setting information linked to at least one of a doctor and a medical practice type specified by the order; and a temporary storage unit configured to temporarily store device setting change information received from the endoscopic system. The endoscopic system has a processing apparatus to which an endoscope is connected. The processing apparatus includes: a second order storage unit configured to store an order received from the medical information management apparatus; a device setting unit configured to make a device setting in accordance with device setting information received from the medical information management apparatus; a second control unit configured to transmit, when a medical practice type is changed while the medical practice specified by the order is being performed, a notification of a change to the medical information management apparatus; and a second operation unit configured to make a device setting of the endoscopic system. When the first control unit receives a notification of a change from the endoscopic system, the first control unit transmits new device setting information corresponding to the change to the endoscopic system. The first control unit displays on a display apparatus a screen for allowing a user to select whether or not device setting information in which the device setting change information stored in the temporary storage unit is incorporated is to be registered in the device setting information storage unit after the medical practice specified by the order is ended. When a device setting of the endoscopic system is changed by an operation signal from the second operation unit while the medical practice specified by the order is being performed, the second control unit transmits device setting change information that indicates a device setting that has been changed to the medical information management apparatus.

Optional combinations of the aforementioned constituting elements and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 3 is a diagram showing an example of an order stored in an order storage unit;

FIG. 4 is a diagram showing an example of a device setting information table stored in a device setting information storage unit;

FIG. 6 is a diagram showing an example of a format for a notification of a change of a medical practice type that is transmitted to the medical information management apparatus from the endoscope processing apparatus;

FIG. 7 is a diagram showing an example of a device setting information prediction table for predicting device setting information after the change of a medical practice type;

FIG. 8 is a diagram showing another example of the device setting information prediction table for predicting device setting information after the change of a medical practice type;

DETAILED DESCRIPTION OF THE INVENTION

The invention will now be described by reference to the preferred embodiments. This does not intend to limit the scope of the present invention, but to exemplify the invention.

Figure 1:
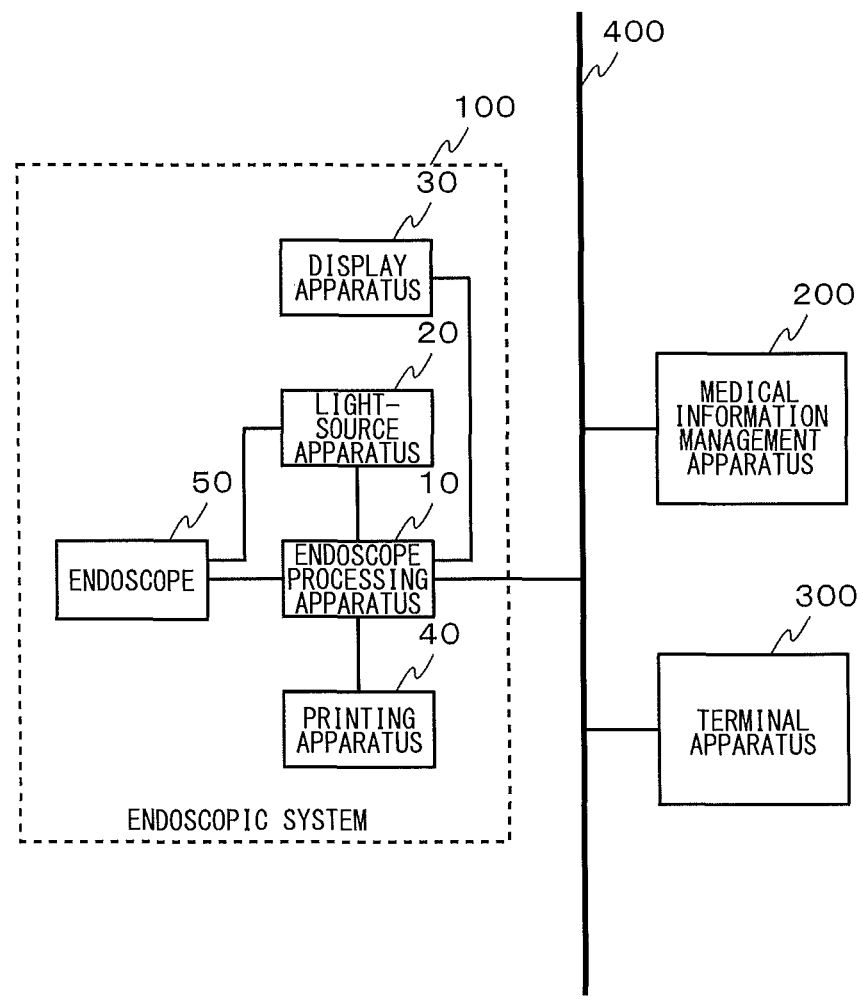
FIG. 1 is a diagram showing the configuration of a medical information management system according to an embodiment of the present invention.

FIG. 1 is a diagram showing the configuration of a medical information management system 500 according to an embodiment of the present invention. The medical information management system 500 according to the present embodiment serves as a system for supporting endoscopic tasks. The medical information management system 500 is provided with an endoscopic system 100, a medical information management apparatus 200, and a terminal apparatus 300, and these are interconnected via a communication line 400. The communication line 400 is assumed to be a wired LAN in the present embodiment. In FIG. 1, only one endoscopic system 100 is drawn. Alternatively, a plurality of endoscopic systems 100 may be connected to the communication line 400. A plurality of endoscopic systems 100 are generally introduced in large-sized hospitals.

The medical information management system 500 can work with another system in a hospital. For example, a gateway apparatus (not shown) is connected to the communication line 400, and the medical information management system 500 can work with an ordering system, an electronic medical record system, and a receipt system via this gateway apparatus. It is assumed in the present embodiment that orders for examination, treatment, and medical care for which the endoscopic system 100 is used are received from the ordering system.

The endoscopic system 100 is provided with an endoscope processing apparatus 10, a light-source apparatus 20, a display apparatus 30, a printing apparatus 40, and an endoscope 50. The endoscope 50 is used by being inserted in a body of a patient. The endoscope 50 captures an image of the inside of the body and outputs the image to the endoscope processing apparatus 10. There are several types of endoscopes 50: those provided with a forceps channel, an air channel, or a water channel. In those types of endoscopes 50, various types of treatment and medical care using treatment tools such as forceps and ESD (Endoscopic submucosal dissection) instruments are possible.

The endoscope processing apparatus 10 controls the entire endoscopic system 100 in a coordinated manner. The endoscope processing apparatus 10 mainly transmits an image captured by the endoscope 50 to the medical information management apparatus 200 and files the image. The light-source apparatus 20 sends light to the inside of the endoscope 50. The display apparatus 30 displays a video image based on a video image signal input from the endoscope processing apparatus 10. The display apparatus 30 mainly displays an image being captured by the endoscope 50 in real time. The printing apparatus 40 prints out data input from the endoscope processing apparatus 10. The printing apparatus 40 mainly prints out image data captured by the endoscope 50.

Figure 2:
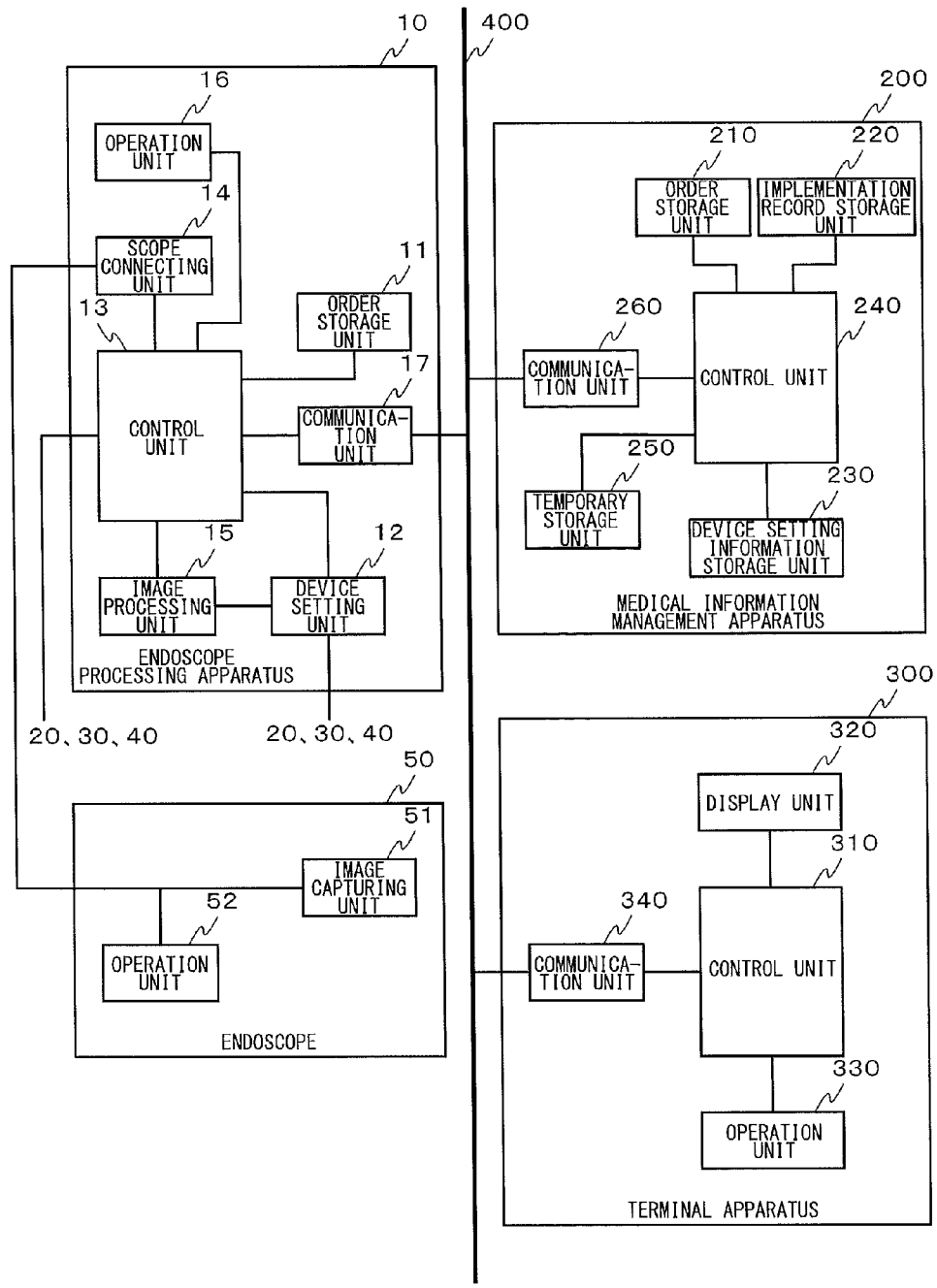
FIG. 2 is a diagram showing the respective configurations of an endoscope processing apparatus, an endoscope, a medical information management apparatus, and a terminal apparatus according to the embodiment of the present invention.

FIG. 2 is a diagram showing the respective configurations of an endoscope processing apparatus 10, a medical information management apparatus 200, and a terminal apparatus 300 according to the embodiment of the present invention. The endoscope 50 is provided with an image capturing unit 51 and an operation unit 52. The image capturing unit 51 is provided with a solid-state imaging device (for example, CCD image sensor or CMOS image sensor) and a signal processing circuit.

The solid-state imaging device converts incident light into an electrical signal. The signal processing circuit performs signal processing such as A/D conversion, noise removal, and the like on an image signal photoelectric-converted by the solid-state imaging device and outputs the image signal to the endoscope processing apparatus 10. The operation unit 52 receives an operation from a doctor who is a user. The operation unit 52 is provided with a release button for image capturing, a dial for adjusting the direction of a tip portion, a control button, and the like. When the control button is pressed down by the doctor, the operation unit 52 outputs an operation signal based on the operation to the endoscope processing apparatus 10.

The endoscope processing apparatus 10 is provided with an order storage unit 11, a device setting unit 12, a control unit 13, a scope connecting unit 14, an image processing unit 15, an operation unit 16, and a communication unit 17. The order storage unit 11 stores an order for a medical practice received from the medical information management apparatus 200. The device setting unit 12 makes a device setting in accordance with device setting information received from the medical information management apparatus 200. More specifically, the device setting unit 12 makes a brightness setting, a size setting, and an effect processing setting for an image captured by the endoscope 50, a setting related to a termination condition for a medical practice, a setting of the amount of light of the light-source apparatus 20, a setting of the display method of the display apparatus 30, a setting of the print method of the printing apparatus 40, and the like. As the effect processing setting, for example, redness, contour enhancement, contrast, and the like are set. These device settings are adjusted based on the type of a medical practice, the condition of an affected part, a doctor's preference, and the like.

The control unit 13 controls the entire endoscope processing apparatus 10 in an integrated manner. The detailed behavior of the control unit 13 will be described later. The scope connecting unit 14 detects the connection of the endoscope 50. Upon detecting the insertion of the endoscope 50 or upon detecting the removal of the endoscope 50, the scope connecting unit 14 outputs a detection signal thereof to the control unit 13. Upon receiving an operation signal from the operation unit 52 of the endoscope 50, the scope connecting unit 14 outputs the operation signal to the control unit 13.

The image processing unit 15 performs various image processing on an image signal input from the endoscope 50. More specifically, the image processing unit 15 performs the brightness adjustment, the size adjustment, and the various types of effect processing described above. In the case of compressing an image so as to record the image, the image processing unit 15 also performs compression encoding. The operation unit 16 receives an operation from a doctor or a nurse and outputs an operation signal based on the operation to the control unit 13. The communication unit 17 performs communication control such that the endoscope processing apparatus 10 becomes connected to the communication line 400.

The medical information management apparatus 200 is constituted of a server in the present embodiment. The medical information management apparatus 200 is provided with an order storage unit 210, an implementation record storage unit 220, a device setting information storage unit 230, a control unit 240, a temporary storage unit 250, and a communication unit 260. The order storage unit 210 stores an order for a medical practice to be performed using the endoscopic system 100. This order is acquired from the ordering system described above.

FIG. 3 is a diagram showing an example of an order stored in the order storage unit 210. An order list 210a shown in FIG. 3 includes a plurality of orders to be performed by the endoscopic system 100. Each order includes an order number, patient information, an examination scheduled date and time, a doctor, an examination room, a medical practice type, a status, etc., as items thereof. In addition to the items shown in FIG. 3, a previous medical history of a patient, an infection, and the like may be included. The patient information includes patient's ID, name, date of birth, age, and sex. Since a doctor is not assigned for order 4, a space is left blank.

It is assumed in the example shown in FIG. 3 that the medical information management system 500 is provided with a plurality of endoscopic systems 100 and that a single endoscopic system 100 is installed in each examination room. Therefore, if an examination room is specified, an endoscopic system 100 to be used to perform a medical practice related to the order is uniquely identified.

FIG. 2 is referred back. The implementation record storage unit 220 stores an implementation record of a medical practice specified by each order. More specifically, the implementation record storage unit 220 stores an endoscopic image captured while the medical practice is being performed, a report created by a doctor, an instrument and a medical agent used for the medical practice, and the like for each order as an implementation record.

The device setting information storage unit 230 stores device setting information for making a device setting of the endoscopic system 100. In the present embodiment, the device setting information storage unit 230 stores device setting information for setting a plurality of device setting items of the endoscopic system 100 all at once.

FIG. 4 is a diagram showing an example of a device setting information table 230a stored in the device setting information storage unit 230. The device setting information table 230a shown in FIG. 4 includes a plurality of pieces of device setting information. Each piece of device setting information includes a master number, master conditions, and setting information. The master conditions include a doctor, a medical practice type, the model number of an endoscope, the model number of an endoscope processing apparatus, the model number of a light-source apparatus, and the model number of a printing apparatus.

Each piece of device setting information is basically a reflection of a doctor's preference. A "doctor" may not be provided as a search key when extracting device setting information from the device setting information table 230a. In this case, the device setting information is extracted from device setting information in which "doctor" is specified to be general.

There are various types of endoscopes. More specifically, there are scopes for upper gastrointestinal tracts, scopes used for lower gastrointestinal tracts, scopes for duodenum, scopes for bronchial tubes, and the like for different parts of a body. Those scopes are further subdivided according to their use or features. For example, upper gastrointestinal tract scopes include general-purpose scopes, narrow-diameter scopes, pernasal scopes, optical magnification scopes, scopes for treatment, and the like. There are also ultrasonic scopes that use ultrasonic waves.

Setting information is defined for each master condition in the device setting information table 230a. Setting information includes the setting information of an endoscope processing apparatus 10, the setting information of a light-source apparatus 20, the setting information of a printing apparatus 40, etc. The setting information of the endoscope processing apparatus 10 includes redness, contrast, image size, termination condition, etc. A termination condition defines a condition for a medical practice specified by a single order to end. In the example shown in FIG. 4, removal of an endoscope 50 from the endoscope processing apparatus 10 and power-off of an endoscope 50 are specified as termination conditions. An action specified in a termination condition serves as a trigger for an order to be closed. The layout setting of the printing apparatus 40 shows the number of images arranged in a single piece of paper.

An aeroperitoneum apparatus is sometimes used for an endoscope examination or endoscopic treatment. An aeroperitoneum apparatus is an apparatus used to inflate intraperitoneal by sending carbon dioxide to the inside of a patient's body. When an aeroperitoneum apparatus that is not shown in FIG. 4 is used, setting information such as the model number of the aeroperitoneum apparatus, pressure, and the like are further included in the device setting information. A method of registering these pieces of device setting information in the device setting information storage unit 230 will be described later.

FIG. 2 is referred back. The control unit 240 controls the entire medical information management apparatus 200 in an integrated manner. The detailed behavior of the control unit 240 will be described later. The temporary storage unit 250 is a work memory for temporarily storing device setting information received from the endoscopic system 100. The communication unit 260 performs communication control for the medical information management apparatus 200 to become connected to the communication line 400.

The terminal apparatus 300 is constituted of a PC in the present embodiment. The terminal apparatus 300 is mainly used for report inputting by a doctor, checking of an endoscopic image that has been captured, processing of registration of device setting information, and the like. The details of a process of registering device setting information will be described later. The terminal apparatus 300 is provided with a control unit 310, a display unit 320, an operation unit 330, and a communication unit 340. The control unit 310 controls the entire terminal apparatus 300 in an integrated manner. The display unit 320 displays information input from the control unit 310. The operation unit 330 includes input devices such as a keyboard, a mouse, and the like. The operation unit 330 receives an operation from a user and outputs an operation signal based on the operation to the control unit 310. The communication unit 340 performs communication control for the terminal apparatus 300 to become connected to the communication line 400.

An explanation is given in the following regarding the device setting of the endoscopic system 100 for a medical practice specified by each order. The control unit 240 of the medical information management apparatus 200 transmits an order to the endoscopic system 100 via the communication line 400 when a predetermined time arrives or when the control unit 240 receives an order acquisition request from the endoscopic system 100. In that case, the control unit 240 transmits device setting information linked to at least one of a doctor and a medical practice type specified by the order.

A detailed description will be given in the following in reference to FIG. 3 and FIG. 4. When transmitting an order to the endoscopic system 100, the control unit 240 of the medical information management apparatus 200 extracts a medical practice type and a doctor included in the order to be transmitted. Using the medical practice type and the doctor that have been extracted as search keys, the control unit 240 searches the device setting information table 230a stored in the device setting information storage unit 230 and extracts device setting information that matches a condition.

For example, when transmitting an order for order number 1 shown in FIG. 3 to the endoscopic system 100, the control unit 240 extracts "upper endoscopic examination" as a medical practice type and "Tanaka" as a doctor from the order. The control unit 240 searches the device setting information table 230a shown in FIG. 4 using "upper endoscopic examination" and "Tanaka" as search keys. The control unit 240 extracts the device setting information for master number 1 from the device setting information table 230a shown in FIG. 4.

There is also a case where a space is left blank for a doctor as in the case of an order for order number 4 shown in FIG. 3. In this case, the control unit 240 extracts only a medical practice type from the order. In this example, "upper endoscopic examination" is extracted as a medical practice type. The control unit 240 searches the device setting information table 230a shown in FIG. 4 using "upper endoscopic examination" as a search key. In that case, only orders in which a doctor is specified to be general are to be searched for. The control unit 240 extracts the device setting information for master number 5 from the device setting information table 230a shown in FIG. 4.

Figure 5:
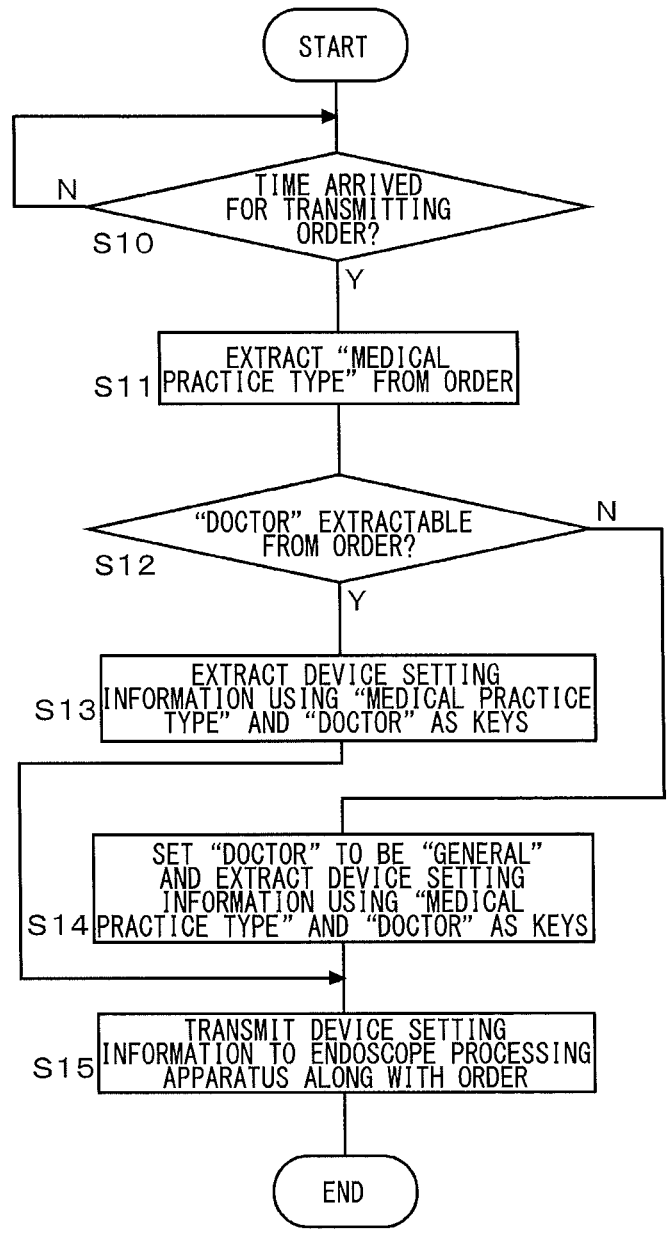
FIG. 5 is a flow chart for explaining a process of transmitting an order and device setting information by the medical information management apparatus according to the embodiment of the present invention.

FIG. 5 is a flow chart for explaining a process of transmitting an order and device setting information by the medical information management apparatus 200 according to the embodiment of the present invention. When a time arrives for transmitting an order (Y in S10), the control unit 240 of the medical information management apparatus 200 extracts a medical practice type from the order to be transmitted (S11). The control unit 240 determines whether or not a "doctor" can be extracted from the order (S12). When a "doctor" can be extracted (Y in S12), the control unit 240 extracts a "doctor" from the order and extracts device setting information that matches a condition from a device setting information table using the medical practice type and the doctor as search keys (S13).

When a "doctor" cannot be extracted (N in S12), the control unit 240 sets a "doctor" to be general and extracts device setting information that matches the condition from the device setting information table using the "medical practice type" and the "doctor" as search keys (S14). The control unit 240 transmits, along with the order, the device setting information that has been extracted to the endoscope processing apparatus 10 (S15).

When receiving the order and the device setting information, the endoscope processing apparatus 10 stores the order and the device setting information in the order storage unit 11. When the order is selected through the operation unit 16 of the endoscope processing apparatus 10, the control unit 13 acquires the device setting information, and the device setting unit 12 makes a device setting in accordance with the device setting information.

An explanation will be given regarding a process of changing device setting information when a medical practice type changes in the middle of a medical practice. When a medical practice type is changed while a medical practice specified by an order is being performed, the control unit 13 of the endoscope processing apparatus 10 transmits a notification of a change to the medical information management apparatus 200. A change in a medical practice type occurs, for example, when a polyp is found in a stomach during an upper endoscopic examination and the poly is to be resected on the spot. In this case, the type changes from upper endoscopic examination to upper endoscopic treatment.

The control unit 13 can recognize a change in a medical practice type by any one of or an optional combination of three methods explained in the following. A first method is for a case where a change in a medical practice type is input by a doctor or a nurse through the operation unit 16 of the endoscope processing apparatus 10. Since this method allows a medical practice type after the change to be transmitted to the medical information management apparatus 200, the medical information management apparatus 200 can easily extract new device setting information to be changed to. Note that the operation unit 16 of the endoscope processing apparatus 10 needs to be provided with a user interface for inputting or selecting a medical practice type after the change. Also, extra work of performing an input operation or a selection operation is required, and a time loss can be easily caused.

FIG. 6 is a diagram showing an example of a format for a notification of a change of a medical practice type that is transmitted to the medical information management apparatus 200 from the endoscope processing apparatus 10. This notification of a change includes as items a doctor, a medical practice type before a change, a medical practice type after the change, and time elapsed since the start of a medical practice.

A second method used for the control unit 13 of the endoscope processing apparatus 10 to recognize a change in a medical practice type is a method of using a detection signal for the removal of an endoscope 50 and a detection signal for the insertion of an endoscope 50 that are input from the scope connecting unit 14. There is a case where an endoscope 50 is changed when a medical practice type is changed. For example, there is a case where the endoscope 50 is changed from a scope used mainly for observation to a scope used mainly for treatment when the medical practice type is changed from upper endoscopic examination to upper endoscopic treatment.

When the scope connecting unit 14 can detect identification information of a scope, the control unit 13 recognizes a change of an endoscope 50 by receiving a detection signal for the insertion of a scope having different identification information from the scope connecting unit 14. When the scope connecting unit 14 cannot detect identification information of a scope, the control unit 13 recognizes a change of an endoscope 50 by receiving a detection signal for the insertion of a scope before the termination of a medical practice and after receiving a detection signal for the removal of a scope from the scope connecting unit 14. In a case of employing this process, a system setting where a medical practice is ended by the pressing of an end key that is provided with the operation unit 16 is required instead of a system setting where a medical practice is ended by the removal or power-off of a scope.

Upon recognizing a change of an endoscope 50, the control unit 13 transmits a notification of a change to the medical information management apparatus 200. This notification of a change does not include a medical practice type after the change as in the case of the first method. When identification information of a scope as changed can be acquired, the identification information is included in a notification of a change.

In the second method, there is no operation burden on a doctor or a nurse, and a notification of a change of a medical practice type can be transmitted to the medical information management apparatus 200 at the same time as an endoscope 50 is changed. However, this method works only for a change of a medical practice type that involves a change of an endoscope 50. Since the types of an endoscope 50 do not always correspond to medical practice types in a one-to-one ratio, it is necessary for the medical information management apparatus 200 to predict a medical practice type after the change.

A third method used for the control unit 13 of the endoscope processing apparatus 10 to recognize a change in a medical practice type is a method of receiving an operation signal from an operation unit 52 of an endoscope 50 via the scope connecting unit 14 so as to recognize a change in a medical practice type based on the operation signal that has been received. For example, a button for changing a medical practice type is provided on an operation unit 52 of an endoscope 50. When the third method is applied to an existing endoscope 50, a function of changing a medical practice type needs to be assigned to an existing button. In this case, when the control unit 13 receives an operation signal through the existing button, the control unit 13 takes the operation signal as an operation of changing a medical practice type.

Upon recognizing a change in a medical practice type based on the operation signal from the operation unit 52 of the endoscope 50, the control unit 13 transmits a notification of a change to the medical information management apparatus 200. This notification of a change does not include a medical practice type after the change as in the case of the first method.

In the third method, operation burdens on a doctor are light, and a notification of a change of a medical practice type can be transmitted to the medical information management apparatus 200 at the same time as an operation button of an endoscope 50 is pressed by the doctor. Note that an operation button is required for an endoscope 50. It is necessary for the medical information management apparatus 200 to predict a medical practice type after the change.

When the control unit 240 of the medical information management apparatus 200 receives a notification of a change of a medical practice type from the endoscopic system 100, the control unit 240 extracts new device setting information according to the change from the device setting information table 230a. When information for specifying a medical practice type after a change is included in the notification of a change, the control unit 240 performs the same process as in the above-described extraction of device setting information when transmitting an order. When information for specifying a medical practice type after a change is not included in the notification of a change, the control unit 240 predicts device setting information to be changed to from device setting information before the change.

An explanation will be given in the following regarding specific example 1 of this prediction method. In specific example 1, a device setting information prediction table 230b for predicting device setting information after a change of a medical practice type is used. Specific example 1 is based on the assumption that identification information of a scope is not included in a notification of a change from the endoscope processing apparatus 10.

FIG. 7 is a diagram showing an example of the device setting information prediction table 230b for predicting device setting information after a change of a medical practice type. This device setting information prediction table 230b is a table for predicting, when a medical practice type is changed while a medical practice is being performed, device setting information to transition to next based on device setting information before the change. FIG. 7 shows an example where a medical practice type before a change is an upper endoscopic examination (general) and where the master number of device setting information that is used is 24.

In general, there are various possibilities for an examination, treatment, or medical care that is to be developed subsequently after an upper endoscopic examination (general). There is, however, a rule of thumb indicating that upper endoscopic treatment is more possible than colonoscopy examinations. The device setting information prediction table 230b defines a subsequent device setting information candidate in descending order of likeliness to be developed subsequently of medical practice types based on such a rule of thumb. Normally, it is considered that there is no change in doctors before and after a change of a medical practice type. Thus, once a medical practice type that is likely to be developed subsequently is identified, device setting information to be employed subsequently can be also specified.

When the control unit 240 of the medical information management apparatus 200 receives a notification of a change of a medical practice type from the endoscopic system 100, the control unit 240 identifies the current device setting information, specifies the subsequent device setting information in reference to the device setting information prediction table 230b, and extracts the subsequent device setting information from the device setting information table 230a. The control unit 240 transmits the device setting information that has been extracted to the endoscope processing apparatus 10.

The control unit 13 of the endoscope processing apparatus 10 receives the device setting information, and the device setting unit 12 makes a device setting in accordance with the device setting information. However, there is a possibility that the prediction of device setting information by the control unit 240 of the medical information management apparatus 200 fails, resulting in an unintended device setting. In that case, the doctor presses the above-stated operation button of the endoscope 50 again. Alternatively, the doctor or the nurse instructs to change the device setting information by operating the operation unit 16 of the endoscope processing apparatus 10. Resulting from this, the control unit 13 of the endoscope processing apparatus 10 transmits a notification requesting a change of the device setting information to the medical information management apparatus 200.

When the control unit 240 of the medical information management apparatus 200 receives a notification requesting a change of a medical practice type from the endoscopic system 100, the control unit 240 excludes the device setting information previously transmitted in reference to the device setting information prediction table 230b and specifies device setting information having a priority next to the previously-transmitted device setting information. The following process is the same as the process of transmitting the previous device setting information.

An explanation is now given of specific example 2 of a prediction method of predicting device setting information to be changed to based on device setting information before a change of a medical practice type. Specific example 2 is based on the assumption that identification information of a scope is included in a notification of a change from the endoscope processing apparatus 10.

FIG. 8 is a diagram showing another example of the device setting information prediction table for predicting device setting information after the change of a medical practice type. This device setting information prediction table 230bb is a table for predicting, when a medical practice type is changed while a medical practice is being performed, device setting information to transition to next based on device setting information before the change and the scope model number after a scope change. FIG. 8 shows an example where a medical practice type before a change is an upper endoscopic examination (general), where the master number of device setting information that is used is 24, and where a scope type after a scope change is AA-02 (for treatment).

If a scope type after a scope change can be identified, a medical practice that is to be performed subsequently can be predicted to some extent. For example, if an upper gastrointestinal tract scope is being inserted, it can be predicted at least that a medical practice to be performed subsequently is not a lower endoscopic examination or an ultrasound examination. In comparison of the device setting information prediction table 230b shown in FIG. 7 with the device setting information prediction table 230bb shown in FIG. 8, although the tables 230b and 230bb have the same previous device setting information, the tables 230b and 230bb have different orders of priority for candidates for subsequent device setting information depending on whether or not a scope type after a scope change is used as an additional parameter.

Figure 9:
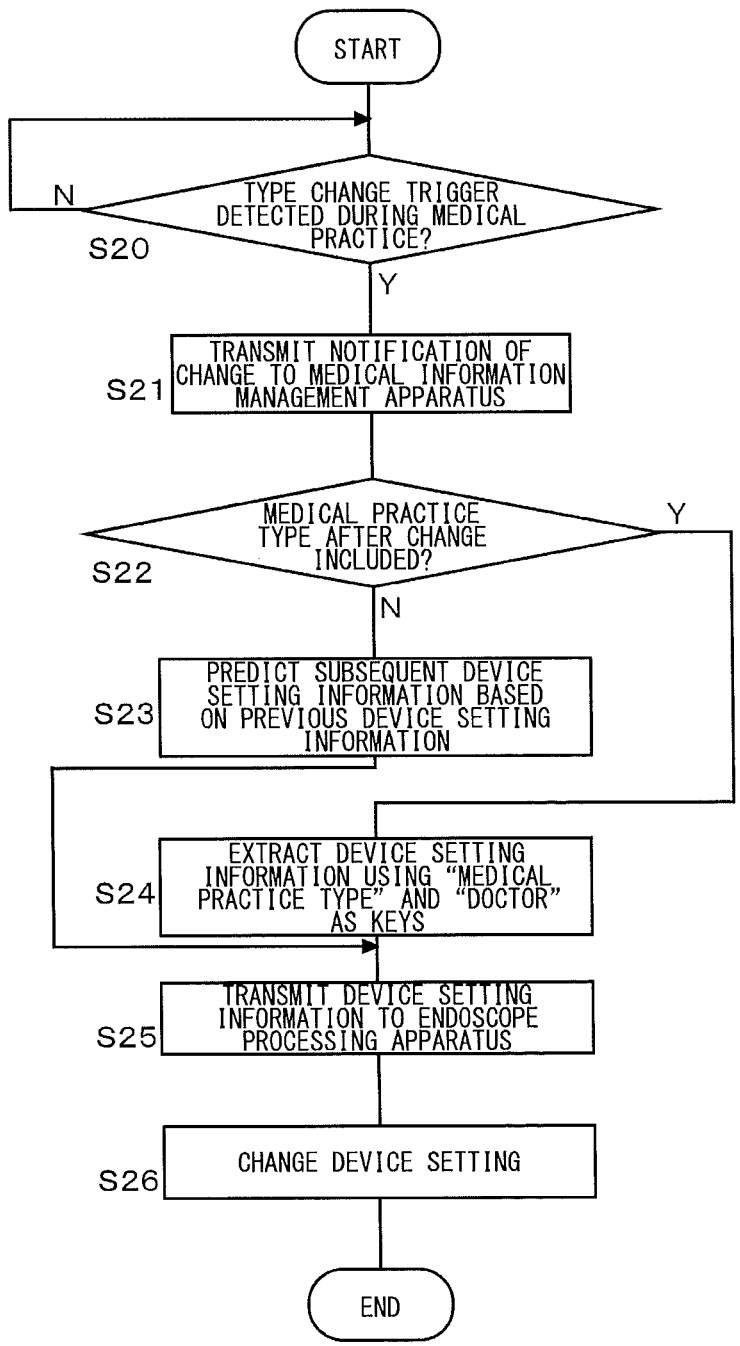
FIG. 9 is a flow chart for explaining a process of transmitting, by the medical information management apparatus according to the embodiment of the present invention, device setting information caused by a change of a medical practice type while a medical practice is being performed.

FIG. 9 is a flow chart for explaining a process of transmitting, by a medical information management system 500 according to the embodiment of the present invention, device setting information caused by a change in a medical practice type during a medical practice. When the control unit 13 of the endoscope processing apparatus 10 detects a medical practice type change trigger in the middle of a medical practice specified by an order (Y in S20), the control unit 13 transmits a notification of a change of a medical practice type to the medical information management apparatus 200 (S21).

The control unit 240 of the medical information management apparatus 200 receives the notification of a change and determines whether or not a medical practice type after the change is included in the notification of a change (S22). When the medical practice type after the change is not included (N in S22), the control unit 240 predicts subsequent device setting information based on the previous device setting information and extracts the subsequent device setting information from a device setting information table (S23). When the identification information of a scope after a scope change is included in the notification of a change, the control unit 240 predicts subsequent device setting information based on the previous device setting information and on a scope model number after the scope change and extracts the subsequent device setting information from the device setting information table.

When the medical practice type after the change is included in the notification of a change in step S22 (Y in S22), the control unit 240 extracts device setting information that matches a condition from the device setting information table using the medical practice type after the change and the doctor as search keys (S24). For the "doctor", a "doctor" used for a search at the time of the transmission of an order is used.

The control unit 240 transmits the device setting information that has been extracted to the endoscope processing apparatus 10 (S25). The control unit 13 of the endoscope processing apparatus 10 receives new device setting information from the medical information management apparatus 200, and the device setting unit 12 changes a device setting in accordance with the device setting information (S26).

An explanation is now given regarding a method of registering device setting information in the device setting information storage unit 230 of the medical information management apparatus 200. There is a case where a doctor wishes to change a device setting while a medical practice is being performed. For example, if a polyp is found in a stomach during an upper endoscopic examination, there may be a case where the strength of contour enhancement is increased and the amount of light of the light-source apparatus 20 is increased.

A doctor or a nurse instructed by the doctor changes a device setting by operating the operation unit 16 of the endoscope processing apparatus 10. If an operation unit for changing the device settings of the light-source apparatus 20, the display apparatus 30, or the printing apparatus 40 is installed in each of the corresponding apparatuses, the doctor or the nurse changes the device setting by operating the operation unit.

When any one of the device settings of the endoscopic system 100 is changed due to an operation signal from the operation unit 16 or from an operation unit of another apparatus while a medical practice specified by an order is being performed, the control unit 13 of the endoscope processing apparatus 10 transmits to the medical information management apparatus 200 device setting change information indicating a device setting that has been changed.

The control unit 240 of the medical information management apparatus 200 stores the device setting change information received from the endoscope processing apparatus 10 in the temporary storage unit 250. The control unit 240 displays a screen for allowing a user to select whether or not device setting information in which the device setting change information stored in the temporary storage unit 250 is incorporated is to be registered in the device setting information storage unit 230 on the display unit 320 of the terminal apparatus 300 after the medical practice specified by the order is ended. The device setting information in which the device setting change information is incorporated means a device setting of the entire endoscopic system 100 obtained at the time when a device setting is changed. The control unit 240 generates the above-stated device setting information in which the device setting change information is incorporated based on the device setting information of the entire endoscopic system 100 immediately before the device setting is changed and on the device setting change information.

As the above-stated screen, the control unit 240 displays, for example, a screen that chronologically describes events from the start to the end of a medical practice including a change of a device setting. Such a registration screen for device setting information is displayed by a user's operation on the operation unit 330 of the terminal apparatus 300. Alternatively, the registration screen may be displayed automatically when a doctor generates a report using the terminal apparatus 300 after a medical practice specified by the order is ended. For example, the above-stated screen may be displayed when a report generation screen is opened or when the report generation screen is closed.

Figure 10:
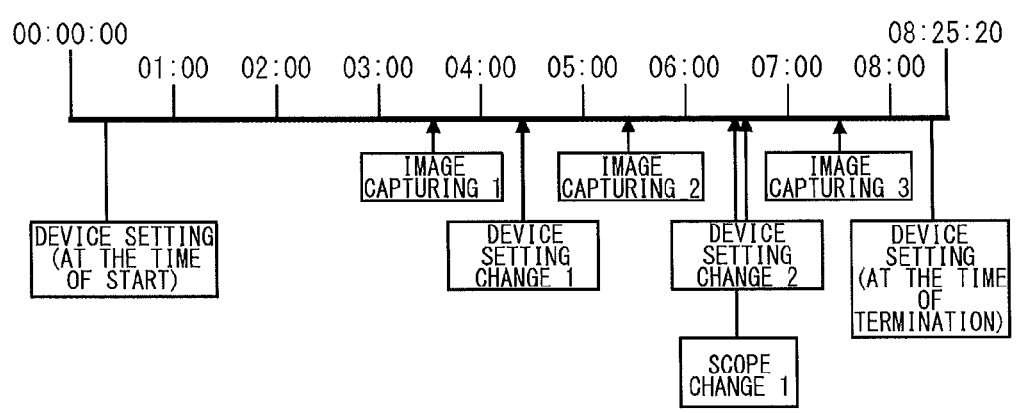
FIG. 10 is a diagram showing an example of a screen chronologically describing events including a change of a device setting.

FIG. 10 is a diagram showing an example of a screen chronologically describing events including a change of a device setting. In a medical practice shown in FIG. 10, a device setting is changed twice, three endoscopic images are captured, and an endoscope 50 is changed once. Looking at this chronological display, the doctor determines whether or not to register a device setting, and, in the case of registering a device setting, the doctor determines a device setting of what point of time is to be registered so as to perform a registration operation.

In FIG. 10, events are shown in characters. Alternatively, events may be shown in icons. For example, an endoscopic image that has been actually captured may be displayed when a cursor for a mouse is moved over an image capturing icon. Also, a list for device setting values at that moment may be displayed in a balloon when the cursor is moved over a device setting icon or a device setting change icon. The screen may transition to a master registration screen through the balloon display. Also, an endoscopic image by a device setting before a change and an endoscopic image by a device setting after a change may be displayed when the cursor is moved over a device setting change icon.

In FIG. 10, in order to be able to master register a device setting at the time of starting a medical practice and a device setting at the time of ending the medical practice, display is shown for selecting the device settings for the both time points. Alternatively, at least one of these displays may be omitted.

Figure 11A:
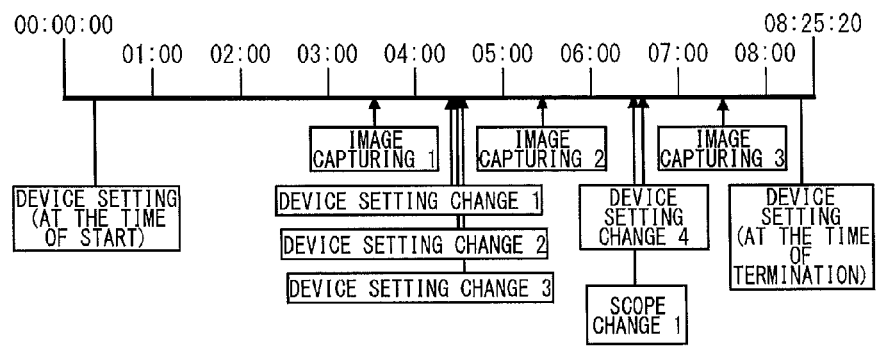
FIGS. 11A-11B are diagrams showing other examples of a screen chronologically describing events including a change of a device setting.
Figure 11B:
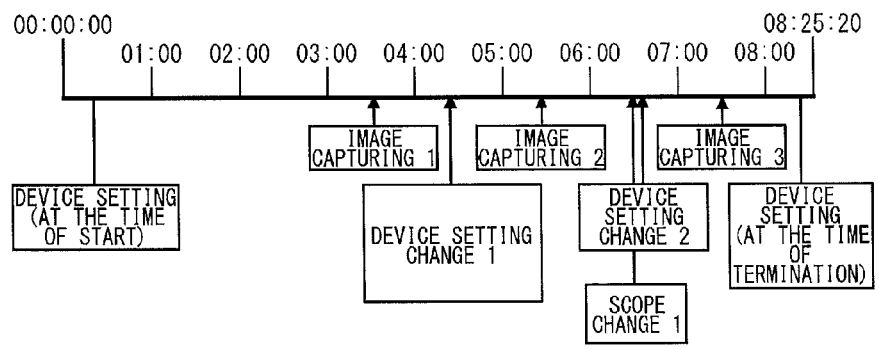

FIGS. 11A-11B are diagrams showing other examples of a screen chronologically describing events including a change of a device setting. In a medical practice shown in FIG. 11A, a device setting is changed four times, three endoscopic images are captured, and an endoscope 50 is changed once. The first three device settings are made almost at the same time. When device settings are made for multiple times within a short period of time, these device settings are considered to be a series of device settings. For example, when settings for redness, contour enhancement, and contrast are changed in a certain situation, it is convenient to treat these changes as a single device setting change. When a single setting item is changed for multiple times within a short period of time, it can be considered that a doctor have reached the most fitting value through trial and error. In this case, it is also convenient to treat these changes as a single device setting change.

FIG. 11B displays a device setting change 1, a device setting change 2, and a device setting change 3 in a medical practice, which are shown in FIG. 11A, together in a form of a single device setting change 1. The control unit 240 of the medical information management apparatus 200 extracts respective change times (may be substituted by reception times) of a plurality of pieces of device setting change information in a certain medical practice that are stored in the temporary storage unit 250. The control unit 240 searches for a combination of pieces of device setting change information that exist within a setting time range (for example, three minutes) based on a plurality of change times that have been extracted. When the combination is detected, the control unit 240 combines pieces of device setting information relating to the combination into one.

Figure 12:
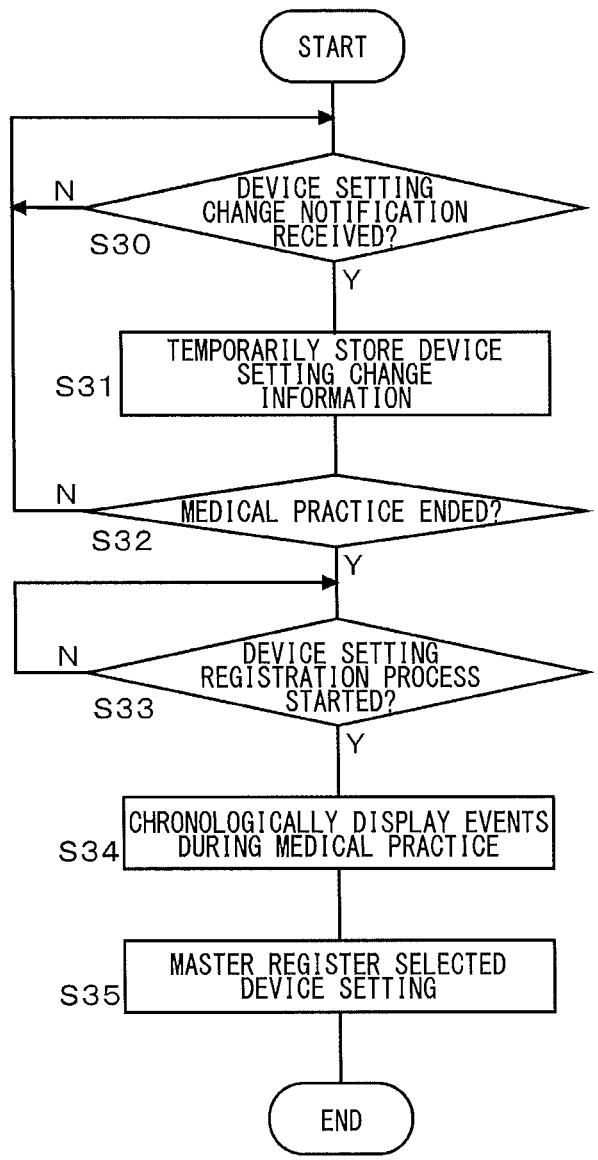
FIG. 12 is a flow chart for explaining a process of registering device setting information by the medical information management apparatus according to the embodiment of the present invention.

FIG. 12 is a flow chart for explaining a process of registering device setting information by the medical information management apparatus 200 according to the embodiment of the present invention. When the control unit 13 of the endoscope processing apparatus 10 detects a change of a device setting made by an operation by a doctor or a nurse instructed by the doctor while a medical practice is being performed, the control unit 13 transmits a device setting change notification including device setting change information to the medical information management apparatus 200. When the control unit 240 of the medical information management apparatus 200 receives the device setting change notification from the endoscope processing apparatus 10 (Y in S30), the control unit 240 temporarily stores the device setting change information included in the notification in the temporary storage unit 250 (S31).

When a device setting registration process is started (Y in S33) after the medical practice is ended (Y in S32), the control unit 240 of the medical information management apparatus 200 chronologically displays events occurred during the medical practice on the display unit 320 of the terminal apparatus 300 (S34). In the device setting information storage unit 230, the control unit 240 of the medical information management apparatus 200 master registers a device setting, among device setting changes that are displayed, that is selection-operated by the doctor (S35).

As explained above, according to the present embodiment, when transmitting an order to an endoscopic system 100, device setting information of the endoscopic system 100 at the time of performing a medical practice specified by the order is transmitted along with the order. In accordance with the device setting information, an endoscope processing apparatus 10 make device settings of the endoscopic system 100 all at once. With this, the labor of a doctor or a nurse instructed by the doctor for manually making a device setting can be saved. This device setting is a reflection of a medical practice type and a doctor's preference. Thus, the doctor can perform a medical practice in a comfortable device setting environment.

There are doctors who do not change a device setting of an endoscopic system 100 according to a medical practice type. If a medical practice is performed under an incorrect device setting of an endoscopic system 100, behavior that is unexpected for the doctor may occur in the endoscopic system 100 while the medical practice is being performed. For example, if a doctor changes an endoscope 50 in the middle of a medical practice when a device setting, in which a termination condition in the device setting information table 230a shown in FIG. 4 is defined to be the removal of a scope, is set, the endoscopic system 100 determines that the medical practice has ended. This also causes the order specifying the medical practice to be closed. If the doctor changes the endoscope 50 without wishing to close the order, the closing of the order caused by the scope change is unexpected behavior for the doctor. If an order is divided without an intention, complicated tasks become necessary such as reissuing of the order, integration of pieces of implementation record data that have been divided, and the like.

If the doctor registers device setting information in which such a setting is removed in advance, a device setting in accordance with the device setting information will be automatically made when the doctor starts the medical practice. Therefore, such a situation can be prevented even without manually changing a device setting.

If a medical practice type is changed in the middle of a medical practice, it is necessary to change a device setting of the endoscopic system 100 in accordance with a medical practice type after the change. In a case where a doctor or a nurse instructed by the doctor manually changes the device setting, it takes time for an operation of changing the device setting. The medical practice is stopped until the operation of changing the device setting is finished. As the stopping of the medical practice becomes longer, a burden on a patient becomes increased. Also, the waiting time for a patient waiting behind becomes longer.

On the other hand, according to the present embodiment, when a medical practice type is changed, a medical information management apparatus 200 that has received a notification of the change transmits to an endoscopic system 100 new device setting information that matches a medical practice type after the change. This allows a device setting of the endoscopic system 100 to be promptly changed, which is necessary when a medical practice type is changed while a medical practice is being performed. This allows for the improvement of the operational efficiency of a medical practice. A burden on the patient and an increase in the waiting time for a patient who is waiting behind that are described above can be prevented. An increase in the working hours of medical staff can be also prevented.

Also, even when an endoscope processing apparatus 10 does not include a medical practice type after a change in a notification of a change of a medical practice type, the use of a device setting information prediction table described above allows a medical information management apparatus 200 to predict device setting information that matches the medical practice type after the change. With this, an operation of inputting the medical practice type after the change performed by a doctor or a nurse can be omitted. The omission of this input operation can lead to an improvement in the operational efficiency of the medical practice.

When a device setting of the endoscopic system 100 is manually changed by a doctor or a nurse instructed by the doctor while a medical practice is being performed, a change of the device setting is transmitted to the medical information management apparatus 200, and the medical information management apparatus 200 temporarily stores the change history of the device setting. This allows the doctor to accurately and easily master register device setting information that has actually been used by the doctor and that the doctor wishes to use again, after the termination of the medical practice.

It is highly necessary to concentrate on a medical practice while the medical practice is being performed. Thus, it is not preferred to master register a change of a device setting on the spot. Thus, one possible option is that the doctor remembers the change of the device setting and master registers device setting information after the termination of the medical practice relying on the memory. However, there is a situation where the device setting cannot be accurately reproduced due to a lapse of memory. Also, an operation of inputting the device setting to the medical information management apparatus 200 using the terminal apparatus 300 is complicated.

In a case of registering device setting information irrespective of an actual medical practice, it often happens that a device setting does not turn out to be a device setting that is expected by the doctor. In this respect, all these problems can be solved according to the present embodiment. Also, by chronologically displaying events that occur during a medical practice, one can easily imagine a device setting of what point in time a device setting of a master registration target is.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

In the above-stated embodiments, master registration is performed on condition that the doctor performs a registration operation when master registering device setting information. In this regard, a control unit 240 of a medical information management apparatus 200 may register a device setting at the time of ending a medical practice in a device setting information storage unit 230 unconditionally as long as there is not the same device setting in device setting information that is already registered in the device setting information storage unit 230. Before confirming the registration, a screen for confirming the registration may be displayed on a display unit 320 of a terminal apparatus 300.

What is claimed is:

1. A medical information management apparatus connected to an endoscopic system via a communication line, comprising:
    an order storage unit configured to store an order for a medical practice to be performed using the endoscopic system;
    a device setting information storage unit configured to store device setting information for making a device setting of the endoscopic system;
    a control unit configured to transmit an order to the endoscopic system via the communication line and also to transmit device setting information linked to at least one of a doctor and a medical practice type specified by the order; and
    a temporary storage unit configured to temporarily store device setting change information received from the endoscopic system,
    wherein when the control unit receives a notification of a change from the endoscopic system while the medical practice specified by the order is being performed, the control unit transmits new device setting information corresponding to the change to the endoscopic system,
    wherein when a device setting of the endoscopic system is changed by a user's operation on the endoscopic system while the medical practice specified by the order is being performed, the control unit receives device setting change information that indicates a device setting that has been changed from the medical information management apparatus, and
    wherein the control unit displays on a display apparatus a screen for allowing a user to select whether or not device setting information in which the device setting change information stored in the temporary storage unit is incorporated is to be registered in the device setting information storage unit after the medical practice specified by the order is ended.

2. The medical information management apparatus according to claim 1,
    wherein the control unit displays a screen that chronologically describes events, including the change of the device setting, from the start to the end of the medical practice specified by the order.

3. A medical information management system comprising an endoscopic system and a medical information management apparatus that are connected to a communication line, wherein the medical information management apparatus has:

a first order storage unit configured to store an order for a medical practice to be performed using the endoscopic system;

a device setting information storage unit configured to store device setting information for making a device setting of the endoscopic system;

a first control unit configured to transmit an order to the endoscopic system via the communication line and also to transmit device setting information linked to at least one of a doctor and a medical practice type specified by the order; and a temporary storage unit configured to temporarily store device setting change information received from the endoscopic system, wherein the endoscopic system has a processing apparatus to which an endoscope is connected, wherein the processing apparatus includes:

a second order storage unit configured to store an order received from the medical information management apparatus;

a device setting unit configured to make a device setting in accordance with device setting information received from the medical information management apparatus;

a second control unit configured to transmit, when a medical practice type is changed while the medical practice specified by the order is being performed, a notification of a change to the medical information management apparatus; and a second operation unit configured to make a device setting of the endoscopic system, wherein when the first control unit receives a notification of a change from the endoscopic system, the first control unit transmits new device setting information corresponding to the change to the endoscopic system, wherein the first control unit displays on a display apparatus a screen for allowing a user to select whether or not device setting information in which the device setting change information stored in the temporary storage unit is incorporated is to be registered in the device setting information storage unit after the medical practice specified by the order is ended, and wherein when a device setting of the endoscopic system is changed by an operation signal from the second operation unit while the medical practice specified by the order is being performed, the second control unit transmits device setting change information that indicates a device setting that has been changed to the medical information management apparatus.

4. The medical information management system according to claim 3, wherein the first control unit displays a screen that chronologically describes events, including the change of the device setting, from the start to the end of the medical practice specified by the order.

\* \* \* \* \*